(12) United States Patent
Hörth et al.

(10) Patent No.: US 8,491,211 B2
(45) Date of Patent: Jul. 23, 2013

(54) DEVICE FOR STORING AND APPLYING LIQUID AND/OR PASTY SUBSTANCES

(75) Inventors: Hans Hörth, Hamburg (DE); Karsten Lamott, Hamburg (DE)

(73) Assignee: Ernst Muhlbauer GmbH & Co., KG, Norderfriedrichskoog (DE)

( * ) Notice: Subject to any disclaimer, the term of this patent is extended or adjusted under 35 U.S.C. 154(b) by 1542 days.

(21) Appl. No.: 12/069,101

(22) Filed: Feb. 7, 2008

(65) Prior Publication Data

US 2008/0170903 A1 Jul. 17, 2008

Related U.S. Application Data

(63) Continuation-in-part of application No. PCT/EP2006/007794, filed on Aug. 7, 2006.

(51) Int. Cl.
*B43M 11/00* (2006.01)
(52) U.S. Cl.
USPC ............................ 401/128; 401/132; 401/183
(58) Field of Classification Search
USPC ................. 401/126, 128–130, 132–134, 118, 401/183
See application file for complete search history.

(56) References Cited

U.S. PATENT DOCUMENTS

| 3,625,349 A | 12/1971 | Muhlbauer |
| 3,739,947 A | 6/1973 | Baumann et al. |
| 4,008,803 A | 2/1977 | Smith |
| 4,952,068 A | 8/1990 | Flint |
| 6,210,059 B1 | 4/2001 | Ramin et al. |
| 6,612,769 B2 * | 9/2003 | Lee et al. ...................... 401/183 |
| 6,685,013 B2 * | 2/2004 | Discko, Jr. ..................... 206/229 |
| 7,467,046 B2 * | 12/2008 | Taylor et al. ..................... 702/19 |
| 2003/0038040 A1 * | 2/2003 | Bertl et al. .................. 206/63.5 |
| 2004/0026282 A1 | 2/2004 | D'Alessio et al. |
| 2004/0104133 A1 | 6/2004 | Aoyagi et al. |
| 2004/0134815 A1 | 7/2004 | Discko, Jr. |

FOREIGN PATENT DOCUMENTS

| DE | 18 02 317 A1 | 5/1970 |
| DE | 20 60 626 A1 | 6/1972 |
| DE | 21 57 492 A1 | 5/1973 |
| DE | 23 24 296 A1 | 12/1973 |
| DE | 25 42 991 A1 | 3/1977 |
| DE | 28 31 005 A1 | 1/1980 |
| DE | 100 22 563 A1 | 11/2001 |

(Continued)

OTHER PUBLICATIONS

English Abstract of Japanese Patent No. JP10250775A, Sep. 22, 1998.

(Continued)

*Primary Examiner* — Huyen Le
(74) *Attorney, Agent, or Firm* — Alix, Yale & Ristas, LLP

(57) ABSTRACT

A device for storing and applying a dental substance, with a container from which the substance can be removed through a first opening in a first direction with the aid of an applicator, and with a substance supply which can be introduced into the container through a second opening in the wall of the container and which is sealed off against this opening by a breakable foil, is characterized in that the second opening is arranged transversely with respect to the first direction and that the foil is applied over the opening in such a manner that it closes same.

46 Claims, 14 Drawing Sheets

FOREIGN PATENT DOCUMENTS

| | | |
|---|---|---|
| DE | 202 08 450 U1 | 12/2003 |
| EP | 0 895 943 A2 | 2/1999 |
| EP | 1 163 918 A | 12/2001 |
| EP | 1 224 925 A2 | 7/2002 |
| EP | 1 459 697 A2 | 9/2004 |
| GB | 2 373 710 A | 10/2002 |
| JP | 10250775 A | 9/2010 |
| JP | 2001340356 A | 12/2011 |
| WO | WO 99/49797 A | 10/1999 |
| WO | WO 01/85569 A | 11/2001 |
| WO | WO2004/028389 A2 | 4/2004 |
| WO | WO2004041673 A1 | 5/2004 |

OTHER PUBLICATIONS

English Abstract of Japanese Publication No. JP2001340356A, Dec. 11, 2001.

English Abstract of PCT Publication No. WO2004041673A1, May 21, 2004.

\* cited by examiner

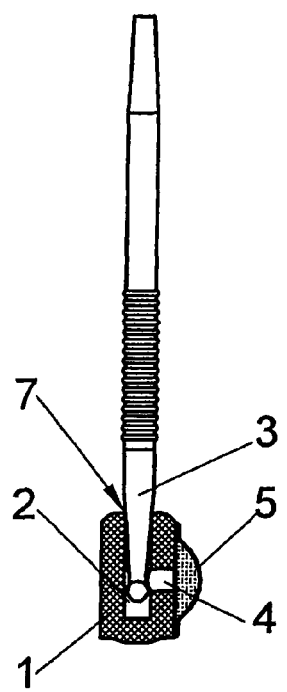
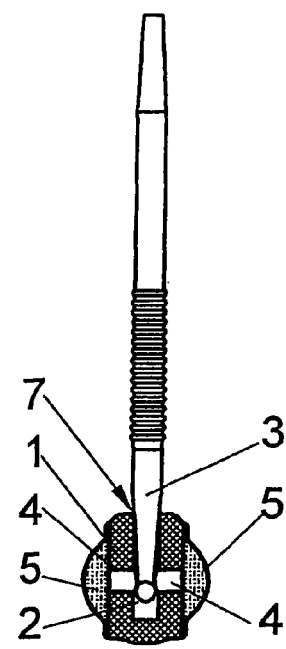
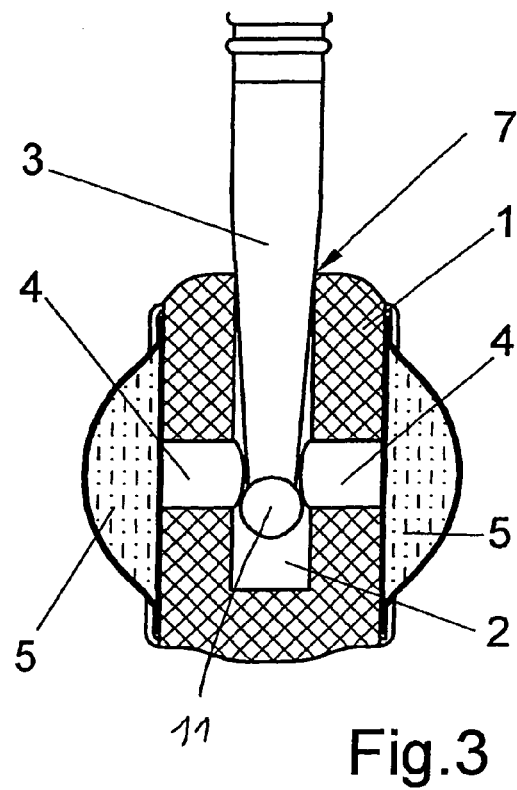

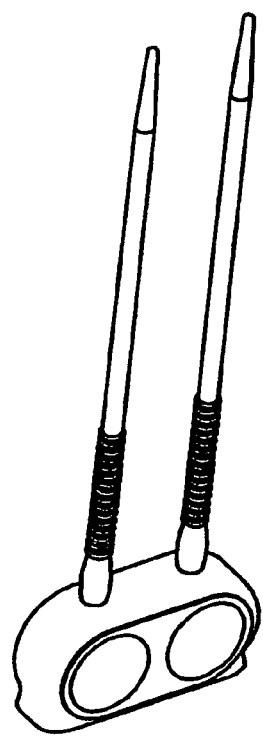 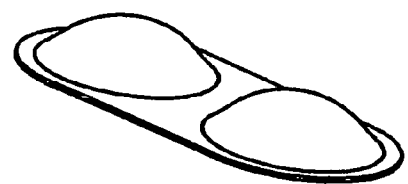
Fig.28  Fig.29
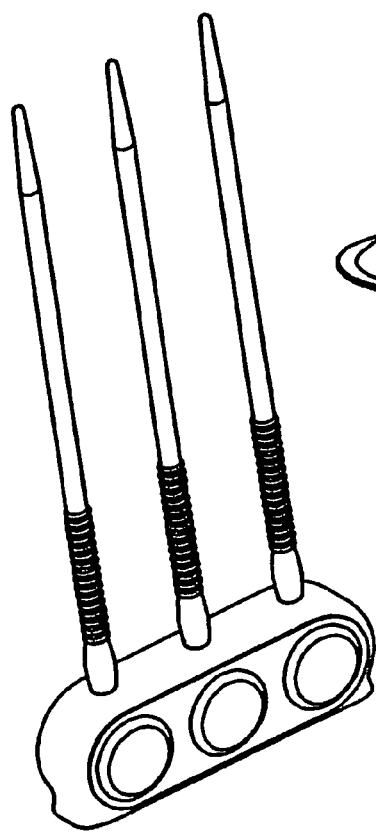 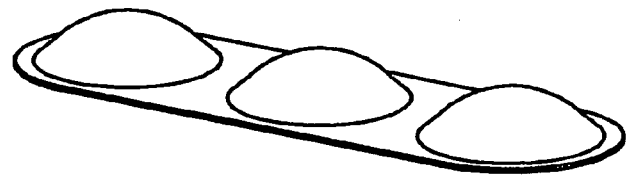
Fig.30  Fig.31

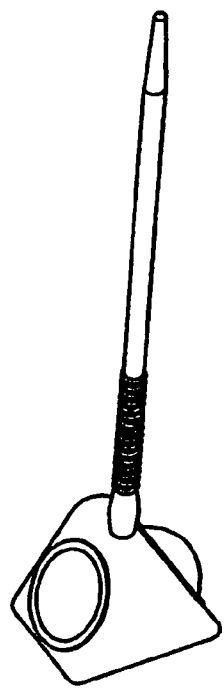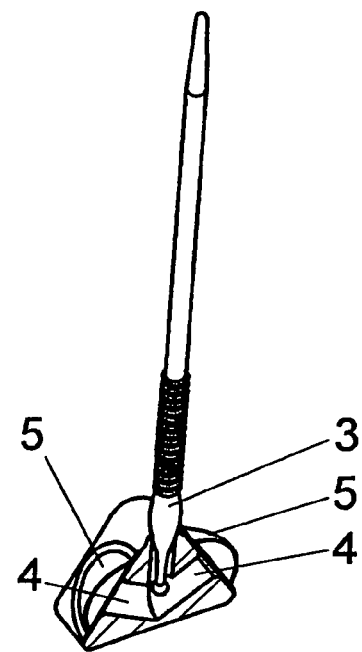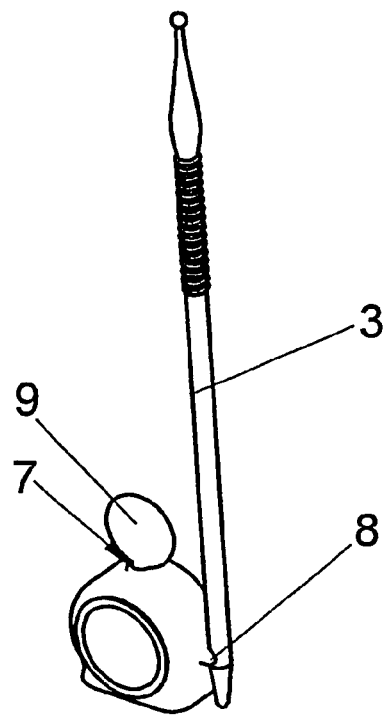
Fig.36　Fig.37
Fig.38

DEVICE FOR STORING AND APPLYING LIQUID AND/OR PASTY SUBSTANCES

CROSS-REFERENCE TO RELATED APPLICATION

This application is a continuation-in-part of International Patent Application No. PCT/EP2006/007794 filed Aug. 7, 2006.

BACKGROUND

The invention relates to a device for storing and applying liquid and/or pasty substances, with a container from which the substance can be removed through a first opening in a first direction with the aid of an applicator, and with a substance supply, which can be introduced into the container through a second opening in the wall of the container and which is sealed off against this opening by a breakable foil.

A known device of this kind (EP 1 163 918 A2) comprises a container which, in a lower part, has one or more foil containers holding the substances. A plunger is pushed into this container and destroys the foil containers. The substance then passes through an opening in the plunger into an interior space of the plunger, where the substance can be removed by an applicator.

This device has various disadvantages. The plunger 2 has to be sealed off from the container 1 since otherwise, when the plunger is pressed into the housing, the substances could escape sideways between container and plunger. If the applicator is intended to be present in the plunger right from the outset and protrudes from the latter (this is expedient in order to protect the mixing space in the plunger from contamination and to obtain a one-piece unit), the protruding part of the applicator gets in the way when pressing the plunger into the container. In any case, it is also disadvantageous when activation and removal take place in the same direction, i.e. the axial direction.

It is known to introduce substances from the side into a mixing space (DE-AS 23 24 296). However, this mixing space is closed; the substance is applied through a nozzle with the aid of a plunger. The use of an applicator that can be introduced into the mixing space is not possible. An object is to make available a device of the aforementioned type which avoids the stated disadvantages and permits better handling.

SUMMARY

The second opening is arranged transversely with respect to the first direction. The substance is therefore pressed from the side into the space in the container, from which it can then be removed from the top with the aid of an applicator. Since pressure is exerted from the side in order to press the substance into the container, and the substance can then be removed from the top, the device does not need to be turned when the substance is introduced into the container. The device is simple and inexpensive to manufacture.

An advantageous embodiment, in which two substances are intended to be mixed, is characterized in that a second substance supply is provided which can be introduced into the container through a third opening arranged diametrically with respect to the second opening and which is sealed off against this opening by a breakable foil. The substances are thus pressed into the container from two opposite sides, so that they are thoroughly mixed together. Since pressure is exerted from both sides on the container, the latter does not need to be specially supported.

Advantageously, at least one substance supply is enclosed in a foil pouch with a breakable foil secured on the second/third opening. This foil pouch is then compressed when the substance is to be brought into the container.

The foil pouch expediently has, on the side directed away from the opening, a stronger foil than on the side directed toward the opening. This ensures that the foil pouch opens on the correct side.

Instead of a foil pouch, provision can also be made for at least one substance supply to be arranged in a cylinder which is closed off with a plunger and which is arranged in front of the second/third opening transverse to the first direction and is sealed off against this opening by a breakable foil. The substance is thus initially enclosed in the cylinder. When pressure is then exerted on the plunger of the cylinder, the breakable foil is opened and the substance flows through the opening into the container.

To ensure that the substance cannot escape sideways between the outer container wall and the foil, provision is expediently made for the breakable foil to be welded or adhesively bonded onto the container. A particularly simple way is for the breakable foil to be flanged, rabbeted or crimped onto the container. It has surprisingly been found that this affords such a secure fit that welding or adhesive bonding is not necessary.

The breakable foil is advantageously provided with a predetermined break point.

The container is expediently made of plastic. It can be produced in particular as an injection-molded part.

The foils are gas impermeable in an advantageous embodiment, so that liquid substances in particular cannot dry out. At least some of the foils are composite foils. These composite foils can comprise an aluminum layer, which promotes the gas impermeability.

The device can on the one hand be designed such that it comprises only one component which is pressed into the container in order to be removed from there with the applicator. However, as has already been mentioned above, it is also possible to provide two components which are then pressed in particular from opposite sides into the container and are mixed together there. However, a third component can also be arranged in the container.

In order to avoid contamination, the first opening can be closed off prior to use, for example by a foil. It is then used with a suitable applicator. However, the device advantageously already comprises an applicator. The latter can be a brush or a sponge. In the case of a brush or sponge, the applicator can be impregnated with a further substance.

The applicator could of course be supplied together with the container, but not initially connected to the container. It is expedient however if the applicator closes the first opening in a leaktight manner. Special sealing means are then not required in order to protect the container from contamination prior to use.

The applicator is expediently conical in the front part since, in dental applications, this makes it easier to apply the substance from the container into the patient's mouth. The applicator can be secured with a form fit on the first opening. In particular, the applicator can be secured on the container with a snap-fit lock connection, so that it can be easily detached for use. The same applies when the container, in another advantageous embodiment, is connected to the container via a predetermined break point.

In one expedient embodiment, a tube for receiving the applicator is provided on the first opening.

The applicator is maintained upright both during the pressing in of the substance/substances and also during removal of the substance from the container with the applicator. If it has a bottom surface for placing it on a base, the container maintains the upright position even when placed on a base. In another advantageous embodiment, the container has a support surface.

As already mentioned, the device can be used for dental purposes. The liquid and/or pasty substances are not however limited to dental substances. The device is suitable also for other areas of application. Devices that may be mentioned, simply as examples of particularly advantageous areas of application, are those which are used for medicine, cosmetics and technical applications such as for adhesives, paints, sealants and other plastic compounds and which are specially designed for these purposes.

BRIEF DESCRIPTION OF THE DRAWINGS

Reference is made to the attached drawings in which:

FIG. 1 shows a first embodiment of the device, partially in cross section,

FIG. 2 shows a second embodiment of the invention, partially in cross section;

FIG. 3 shows an enlarged representation of the embodiment from FIG. 2;

FIGS. 4-39 show further embodiments;

DETAILED DESCRIPTION OF THE PREFERRED EMBODIMENTS

Figure 4:
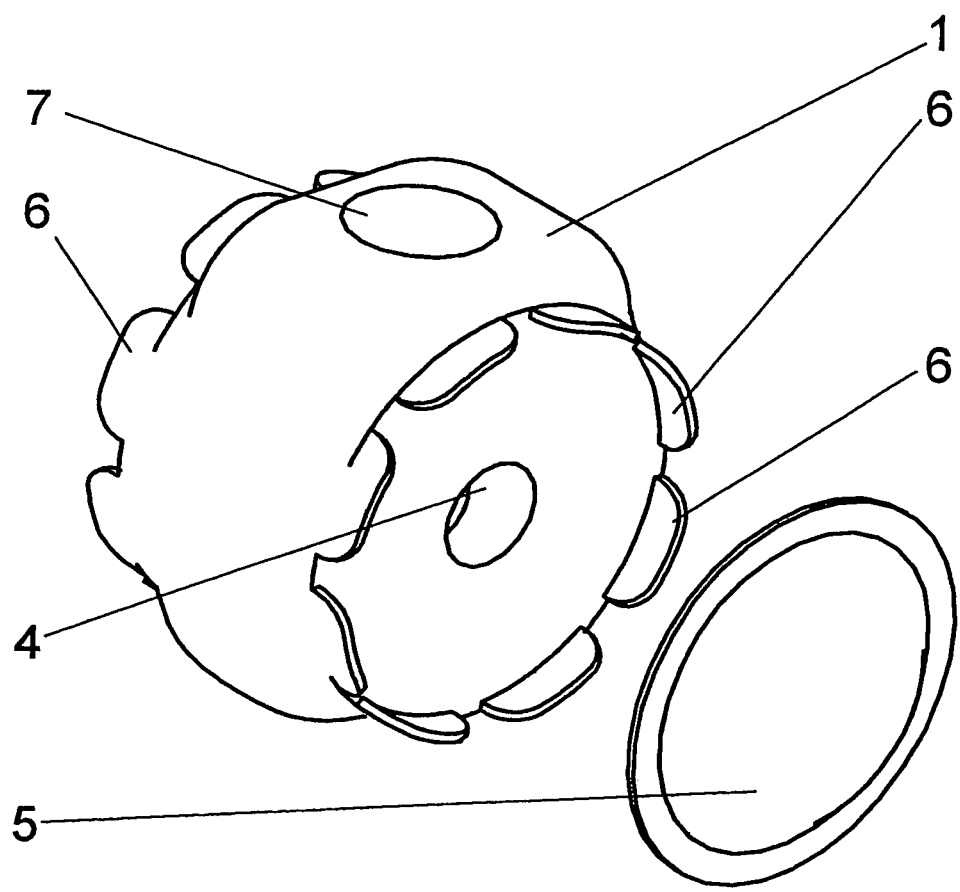

As is shown in FIG. 1, the device comprises a container 1 with a hollow space 2 and with a first opening 7 into which an applicator 3 is inserted or can be inserted. Provided in the wall perpendicular to the extent of the applicator 3 there is a further opening 4 over which a foil pouch 5 is secured which contains the substance that is to be applied. When the foil pouch 5 is compressed, the substance contained in it flows through the opening 4 into the space 2 and can be removed by the applicator 3. The container 1 is an injection-molded part preferably composed of plastic.

In the embodiment in FIG. 2, the container 1 is provided with two further openings 4 which are diametrical with respect to one another and transverse to the longitudinal extent of the applicator 3 and over which foil pouches 5 are secured. By compression of the foil pouches 5, the substances in the latter can be brought into the space 2 and mixed together and can then be removed by the applicator 3.

FIG. 3 shows an enlarged representation of the embodiment in FIG. 2. Here (and in the further figures) an element 11 is also shown schematically with which the components can be applied. This can in particular be a brush, a sponge or a spatula. The spatula is of course particularly suitable for applications where pasty substances are used.

In the embodiments in FIGS. 1-3, the container is substantially rectangular. FIG. 4 shows an embodiment in which the container 1 is substantially round. After the foil pouch 5 has been fitted on the container 1, projections 6 about the edge of the foil pouch 5 can be flanged or rabbeted in order to securely hold the foil pouch 5.

Figure 5:
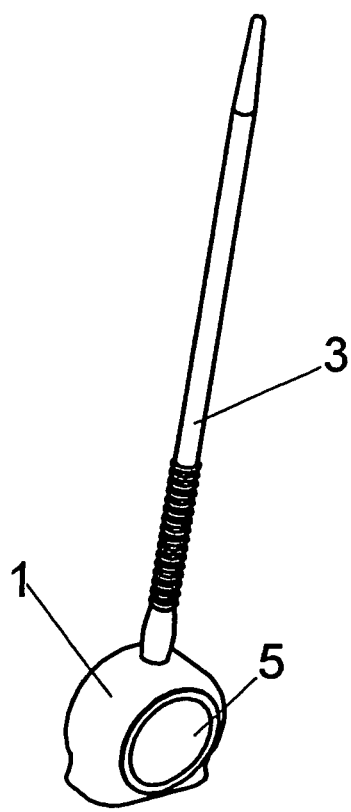
Figure 6:
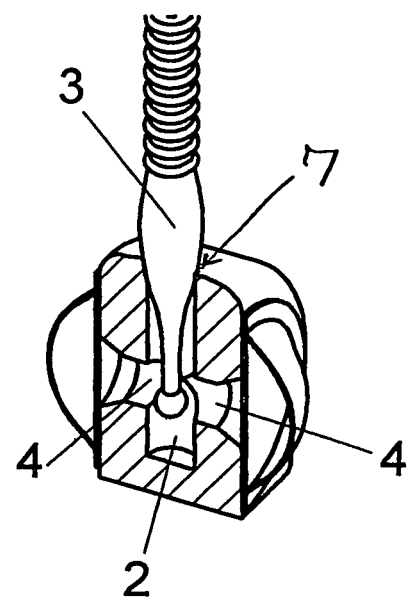

FIG. 5 shows a perspective view of a preferred embodiment. FIG. 6 shows this embodiment enlarged and partially in cross section.

Figure 7:
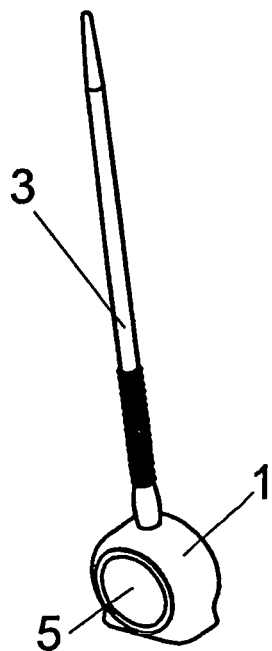
Figure 8:
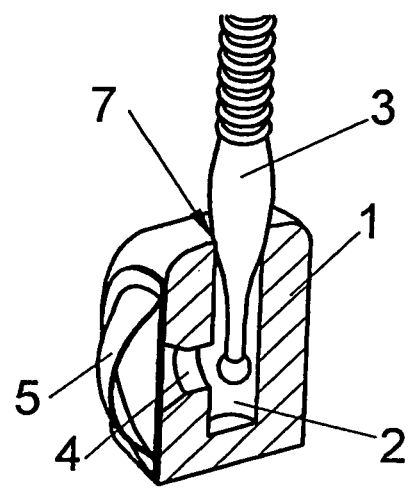

FIGS. 7 and 8 show, in similar representations as in FIGS. 5 and 6, a perspective overall view and an enlarged sectional view, respectively, of an embodiment that has only one substance supply.

Figure 9:
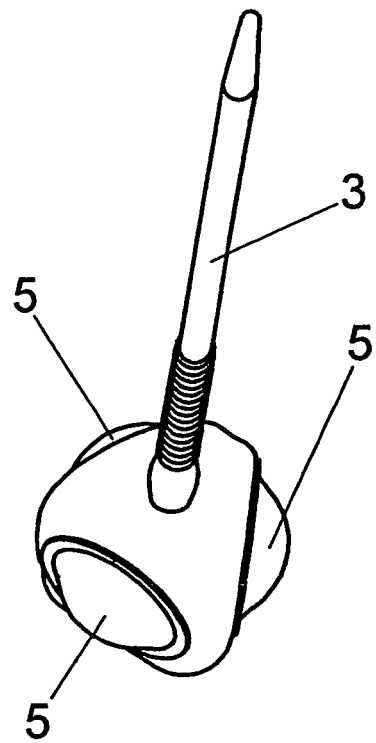
Figure 10:
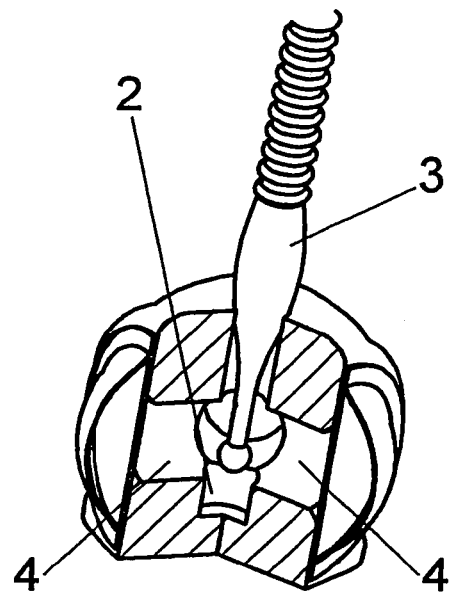

FIGS. 9 and 10 show again a perspective view and a partially cross-sectional view, respectively, of a further embodiment which is designed like a triangle in such a way that three foil pouches 5 can be applied, for example welded on. Behind each of the foil pouches 5 there is once again a bore 4. The three bores 4 meet in the center of the hollow space 2, such that the individual liquids are brought together after the foil pouches 5 are burst.

Figure 11:
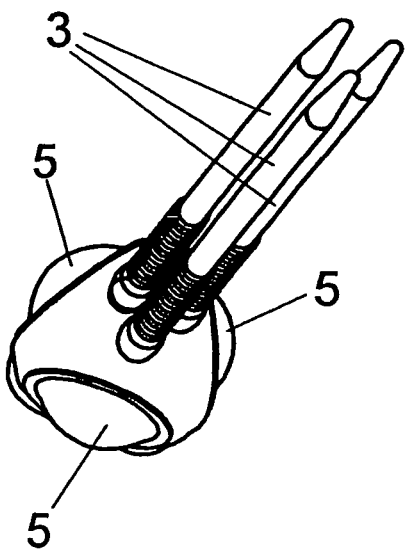
Figure 12:
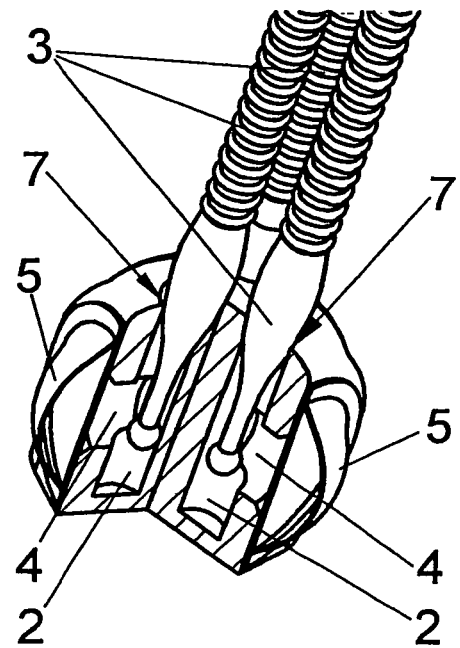

FIGS. 11 and 12 also show a container 1 configured with three sides. To be able to apply all three components separately and in succession, the bores 4 behind the foils 5 are not interconnected, in contrast to the embodiment in FIGS. 9 and 10. Consequently, in this embodiment three first openings 7 are provided with three hollow spaces 2 and three applicators 3.

Figure 13:
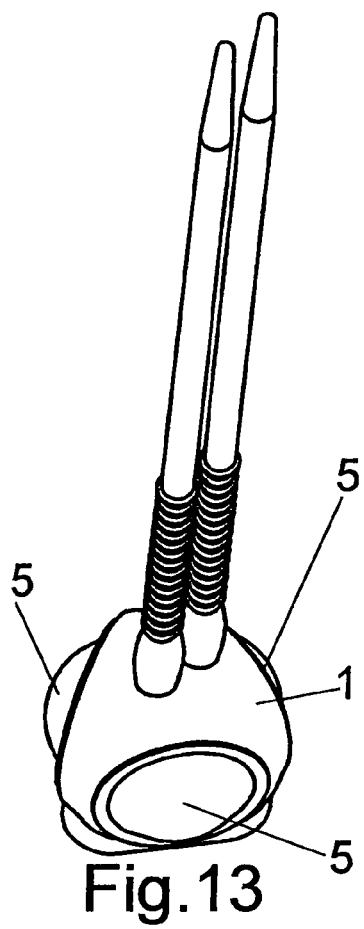
Figure 14:
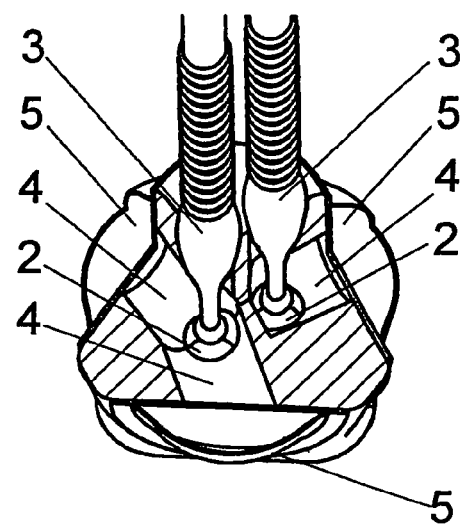

FIGS. 13 and 14 show an embodiment with two separate hollow spaces 2 and applicators 3 arranged therein. The left-hand hollow space in the figure is provided with two openings 4 and foil pouches 5 whose contents can be mixed together in the hollow space 2. The right-hand hollow space 2 is provided with only one opening 4 and one foil pouch 5, so that here only one component can be removed by the applicator 3.

Figure 15:
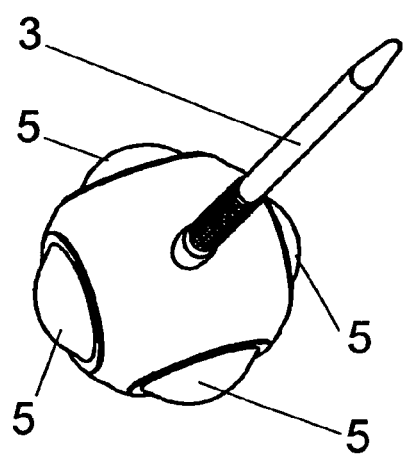
Figure 16:
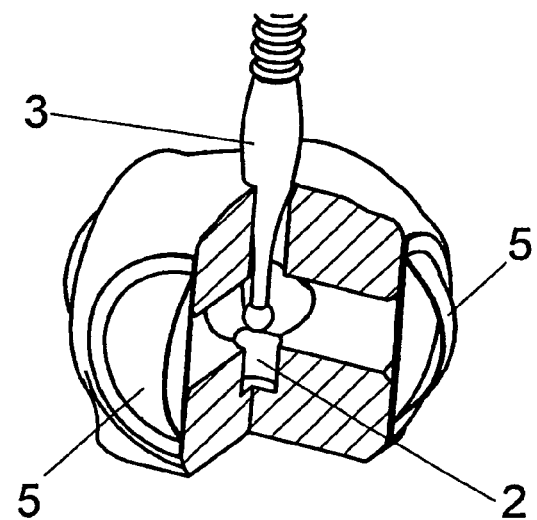

FIGS. 15 and 16 show an embodiment with four foil pouches 5 whose associated openings 4 all lead into the hollow space 2, so that the four components can be mixed together.

Figure 17:
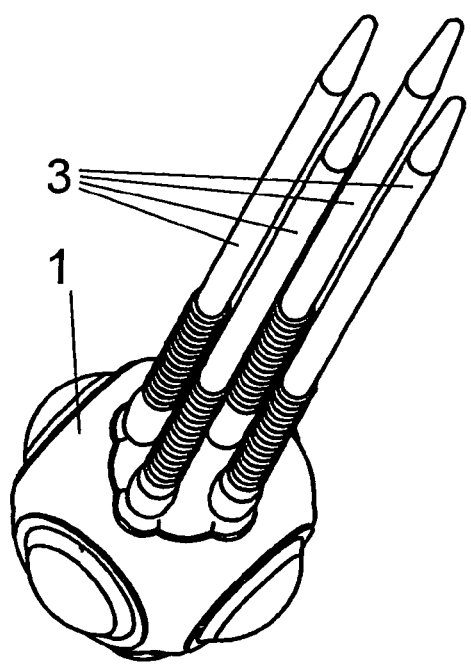
Figure 18:
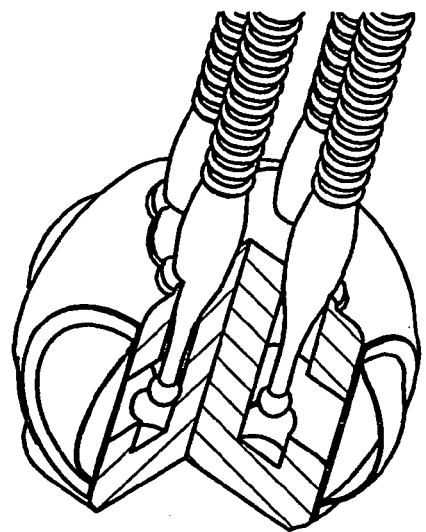

In the embodiment in FIGS. 17 and 18, four foil pouches 5 are once again provided which each lead into the hollow space 2. The hollow spaces 2 are separated from one another and are each provided with a separate applicator 3. Four liquids or pastes can therefore be removed independently of one another which cannot be mixed together in the container 1.

Figure 19:
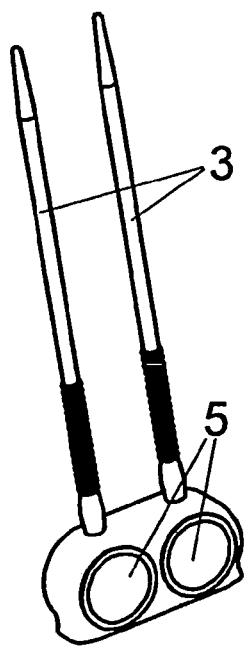
Figure 21:
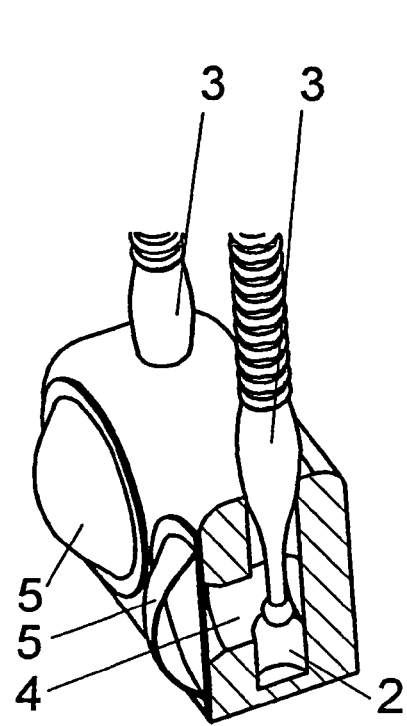
Figure 20:
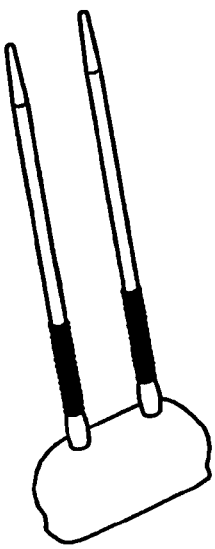

FIGS. 19 and 20 show a further embodiment from the front and back, respectively. An enlarged partially cross-sectional view of this embodiment is shown in FIG. 21. The container 1 in this case has two interconnected areas which each comprise separate systems of foil pouch 5, opening 4, hollow space 2 and applicator 3. However, each hollow space 2 is supplied only by the content of one foil pouch 5; the individual components are not mixed together.

Figure 22:
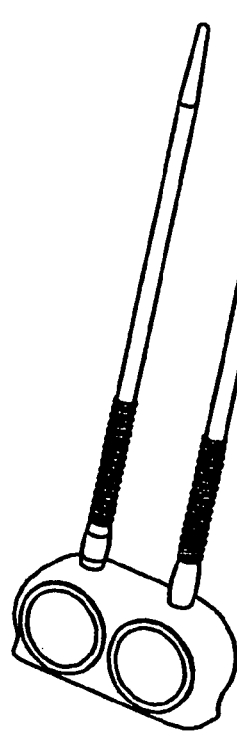
Figure 23:
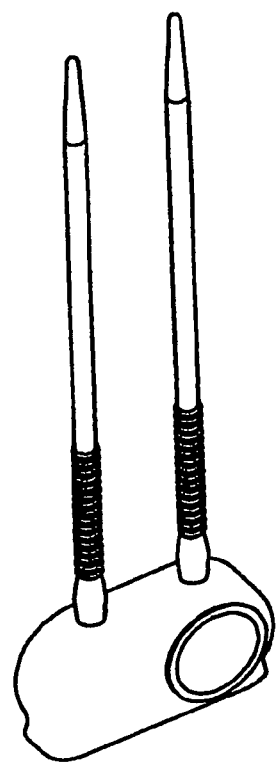
Figure 24:
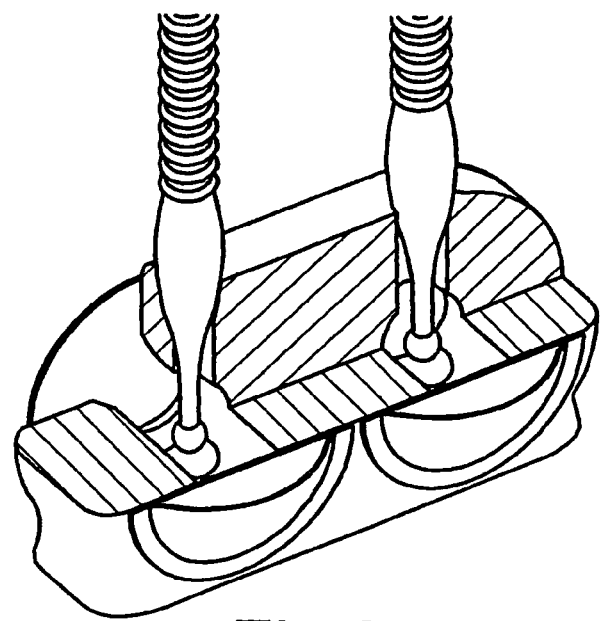

FIGS. 22-24 show a further embodiment in a similar representation to that of FIGS. 19-21. The embodiment has two areas which are mechanically interconnected but which, in flow terms, are separate from one another. One area is provided with two foil pouches 5, so that here two components can be mixed, whereas the second area has only one foil and only one substance supply.

Figure 25:
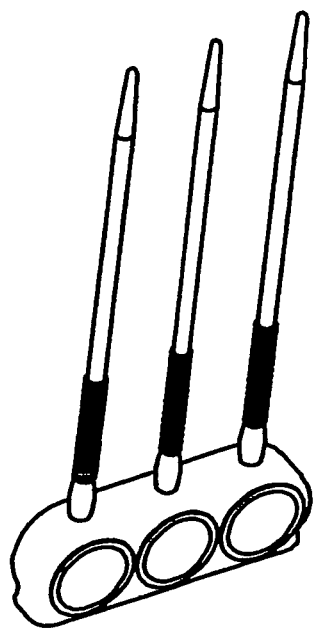
Figure 26:
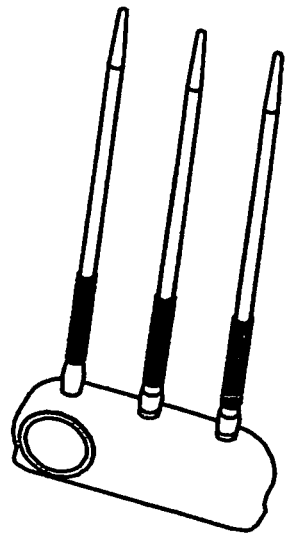
Figure 27:
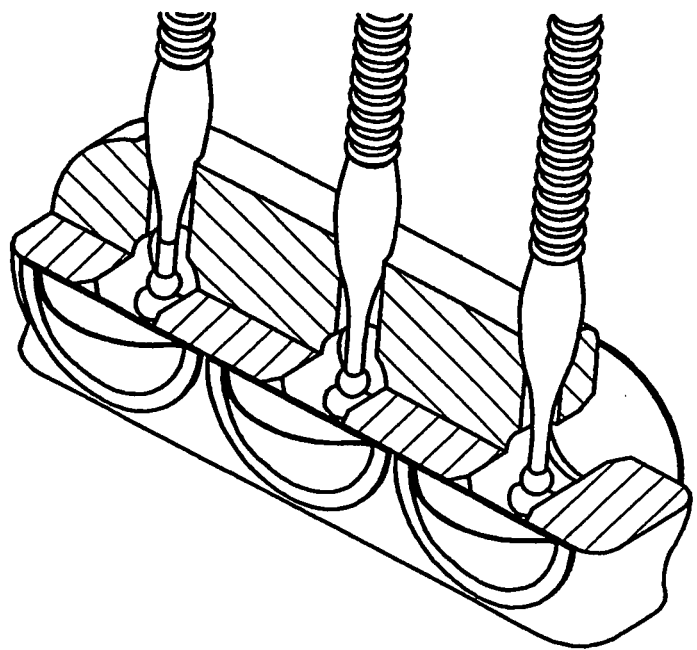

The embodiment in FIGS. 25-27 has three areas arranged alongside one another. In one area, the substance supplies of two components can be mixed with one another, whereas for the other areas only one foil pouch 5 is in each case provided, so that here only one individual component can be removed.

FIGS. 28 and 30 show further embodiments in which the foil pouches lying alongside one another are connected to one another in one piece, as is shown more clearly in FIGS. 29 and 31.

Figure 32:
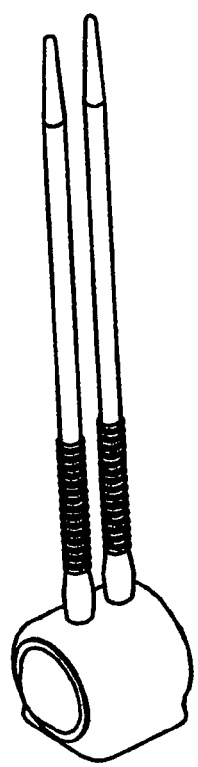
Figure 33:
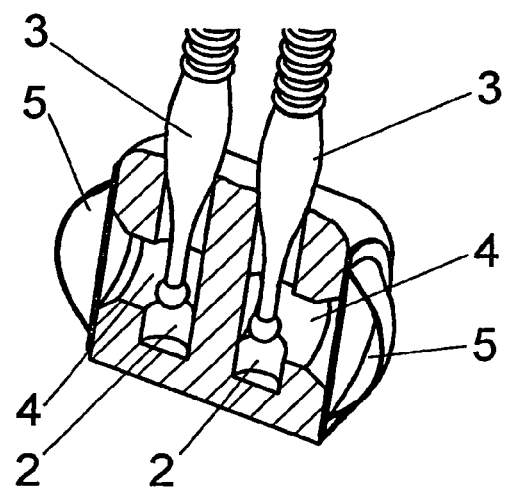

FIGS. 32 and 33 show an embodiment in which the two hollow spaces 2 and the applicators 3 are arranged behind one another. Each hollow space 2 is provided with an opening 4 and a foil pouch 5. One component can therefore be removed independently of another.

Figure 34:
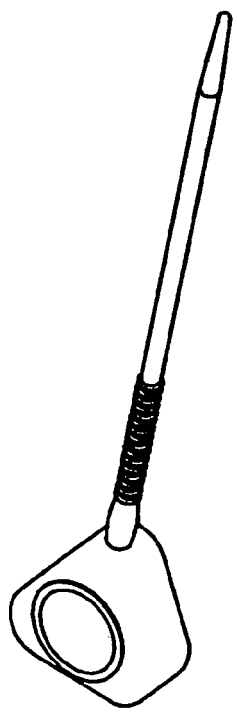
Figure 35:
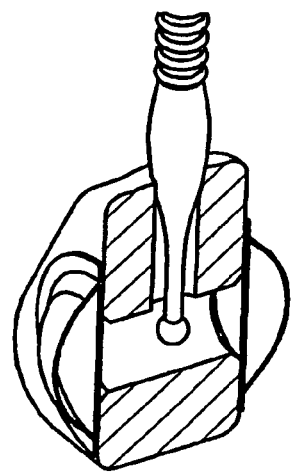

The embodiment in FIGS. 34 and 35 corresponds in function to the embodiment in FIGS. 5 and 6 but has a triangular shape.

The embodiment in FIGS. 36 and 37 again has, like the pre-ceding embodiment, a triangular shape. Here, however, the foil pouches 5 and the openings 4 are arranged on inclined side faces.

The embodiment in FIG. 38 has a snap-fit lock device 8 on which the applicator 3 can be secured. The hollow space 2 is in this case closed by a stopper 9 in order to avoid its contamination. This stopper 9 is removed when the applicator 3 is inserted into the opening 7.

Figure 39:
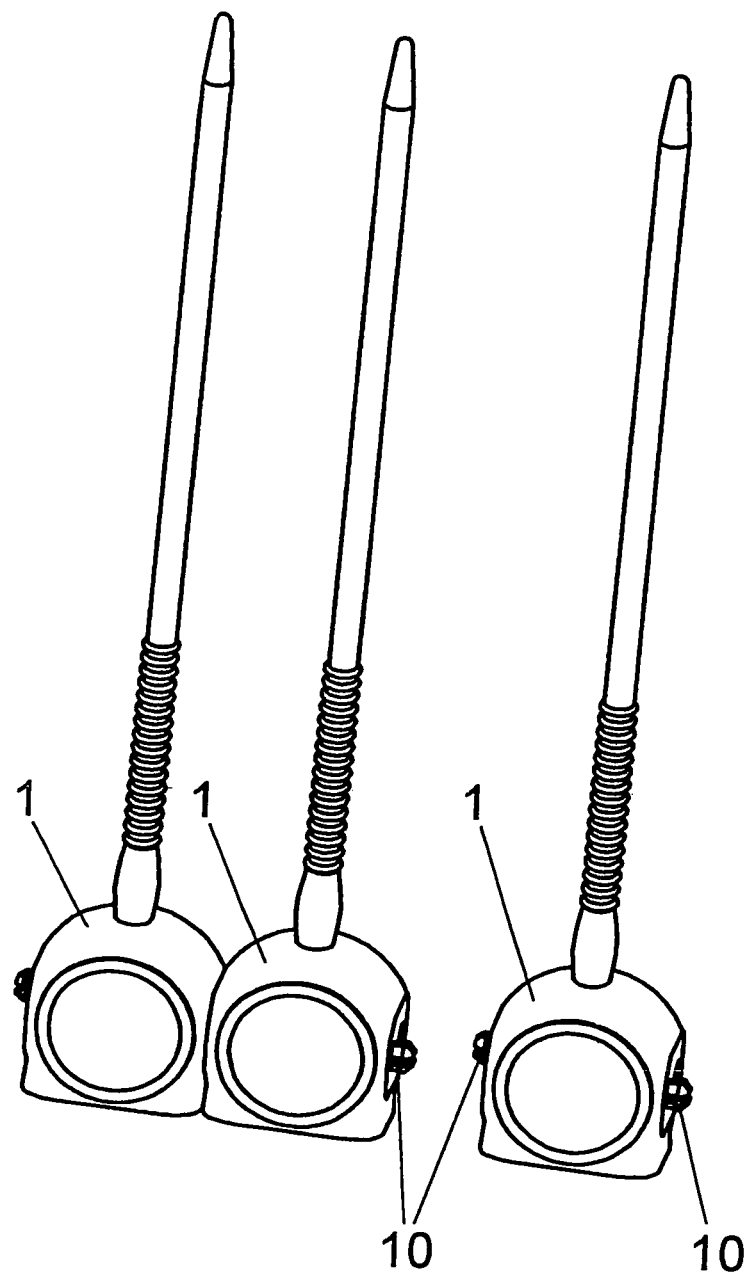

The embodiment in FIG. 39 has several containers 1 which have snap-fit lock devices 10 with which they can be connected to one another.

The foils may be gas permeable. At least some of the foils may be composite foils which have an aluminium layer.

Figure 42:
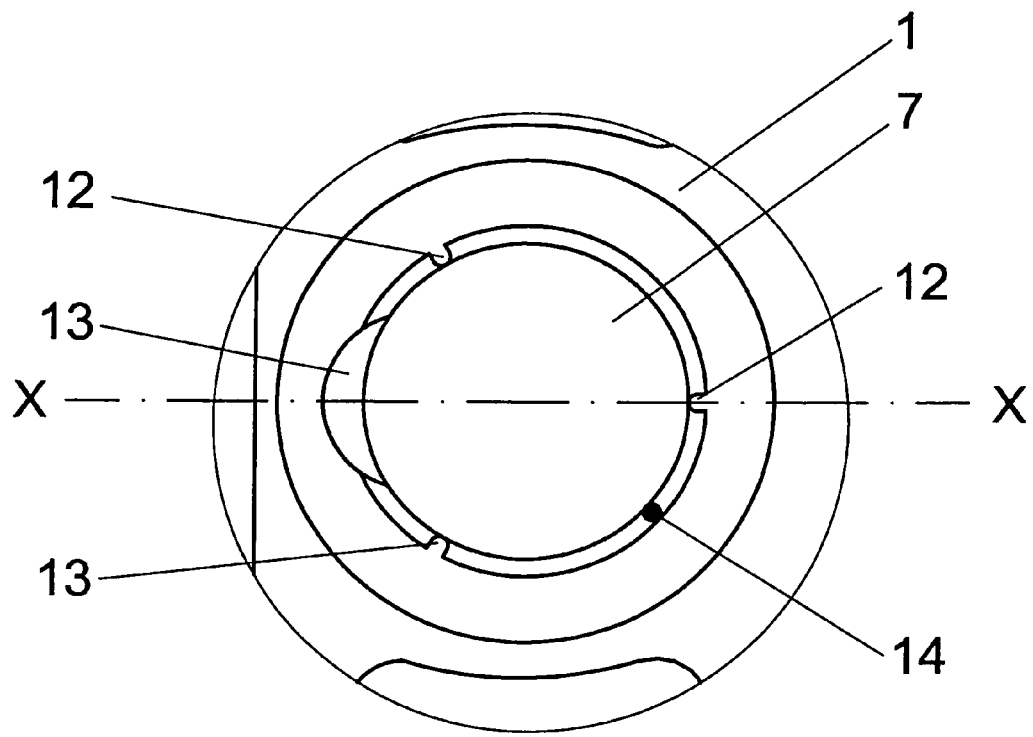
FIG. 42 shows the embodiment of FIGS. 40 and 41 in a top view in enlarged scale.

The embodiment of FIGS. 40 through 47 in the region of the opening is provided with axial extending ribs 12 for supporting the applicator 3. As can be seen in FIG. 42 between the applicator 3 and the wall of opening 7 in this manner arcuate slits are left open. When the substance is pressed into the container 1, air can escape from the container through these arcuate slits. In addition, a venting channel 13 is provided.

Figures 40, 41:
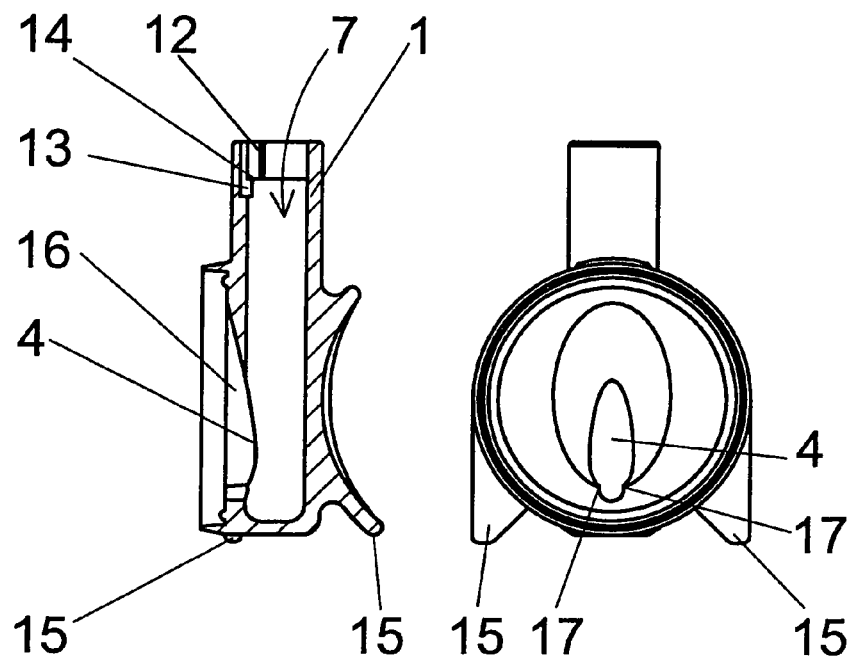
FIG. 40 shows a further embodiment in cross section along line X-X of FIG. 42.
FIG. 41 shows a side view of the embodiment of FIG. 40.

In FIGS. 40 and 42 a stop 14 for the applicator 3 is shown which limits the movement of the applicator 3 into the container 1. As can be seen in FIGS. 40 and 41, the container 1 has three bottom protrusions 15 which serve as a three-point support for holding the container 1 on a surface thus saving material.

As shown in FIGS. 40 and 41 the second opening 4 is surrounded by a trough or depression 16 in the wall of the container 1. This depression 16 has the largest depth in the vicinity of the second opening 4. The opening 4 can be provided with cutting edges 17.

The purpose is as follows.

After the foil pouch 5 has been affixed to the container 1, (FIGS. 43 and 44) pressure is exerted in the direction of arrow 18. Due to the special form of the depression 16 the foil pouch 5 is stressed and deformed to the maximum extent in the region of the second opening 4 and will rupture here. This will also result in a popping sound indicating that the substance has been transferred into the inner space of container 1.

Figures 43, 44, 47:
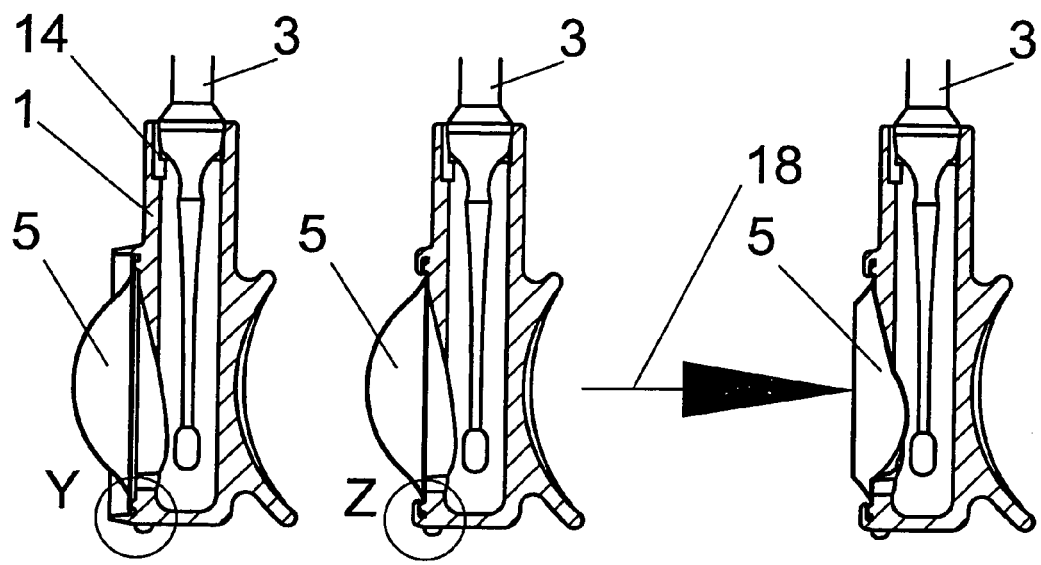
FIGS. 43 and 44 show the embodiment of FIGS. 40 and 41 with inserted applicator and foil pouch.
FIG. 47 shows the embodiment of FIGS. 40 through 46 during the application.
Figures 45, 46:
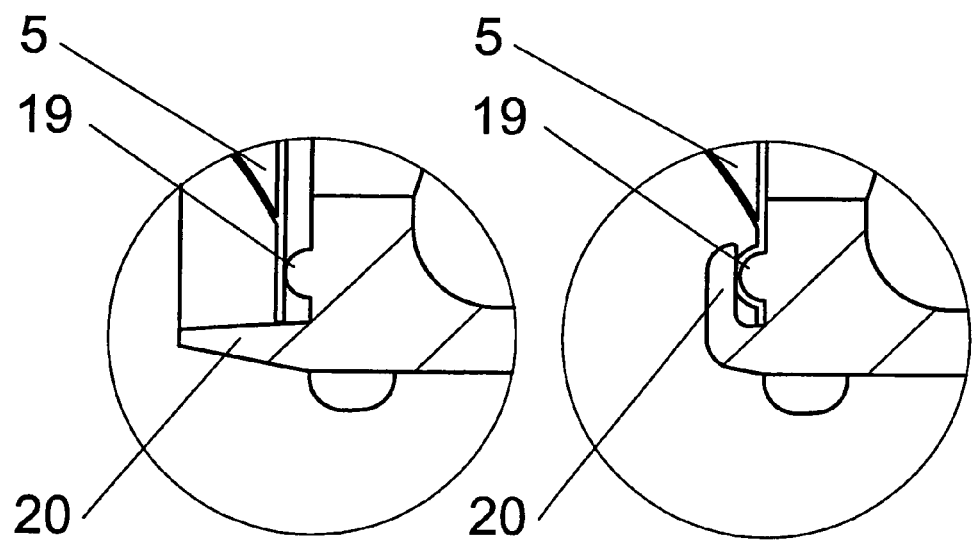
FIGS. 45 and 46 show details Y and Z of FIGS. 43 and 44.

As can be seen in FIGS. 43 and 45, container 1 has annular protrusions 19 and 20. As best seen in FIG. 46, the foil of the pouch 5 can be crimped between these two protrusions thus obtaining a tight seal in this region.

The invention claimed is:

1. A device for storing and applying liquid and/or pasty substances, with an applicator, with an injection-molded container from which the substance can be removed through a first opening in a first direction with the aid of the applicator, and with a substance supply which can be introduced into the container through a second opening in a wall of the container and which is sealed off against the second opening by a breakable foil, characterized in that the applicator is insertable into and removable from the first opening and that the second opening is arranged transversely with respect to the first direction and that the foil is applied over the second opening in such a manner that it closes the opening, wherein the first and second openings are in fluid communication with the same space in the container from which the substance can be removed, and upon breaking the foil the substance flows through the second opening into the hollow space of the container in a direction transverse to the first opening.

2. The device as claimed in claim 1, characterized in that a second substance supply is provided which can be introduced into the container through a third opening arranged diametrically with respect to the second opening and which is sealed off against this opening by a breakable foil.

3. The device as claimed in claim 2, characterized in that at least some of the foils are composite foils.

4. The device as claimed in claim 3, characterized in that the composite foils have an aluminum layer.

5. The device as claimed in claim 1, characterized in that more than two substance supplies are provided which can be introduced into the container through further openings arranged transversely with respect to the first direction and which are sealed off against this opening by in each case a breakable foil.

6. The device as claimed in claim 5, characterized in that three substance supplies are provided.

7. The device as claimed in claim 5, characterized in that four substance supplies are provided which can be introduced into the container through openings arranged in each case diametrically with respect to an opposite opening and which are sealed off against their opening by a breakable foil.

8. The device as claimed in claim 1, characterized in that at least one substance supply is enclosed in a foil pouch with a breakable foil secured on the second opening.

9. The device as claimed in claim 8, characterized in that the foil pouch, on the side directed away from the second opening, has a stronger foil than on the side directed toward the second opening.

10. The device as claimed in claim 8, characterized in that the foil pouch contains an aluminum layer coated with an outer resin layer.

11. The device as claimed in claim 1, characterized in that the breakable foil is welded onto the container.

12. The device as claimed in claim 1, characterized in that the breakable foil is adhesively bonded onto the container.

13. The device as claimed in claim 1, characterized in that the breakable foil is flanged, rabbeted or crimped onto the container.

14. The device as claimed in claim 1, characterized in that the breakable foil is provided with a predetermined break point.

15. The device as claimed in claim 1, characterized in that the foil is gas impermeable.

16. The device as claimed in claim 1, characterized in that at least one substance supply is arranged in a cylinder which is closed off with a plunger and which is arranged in front of an opening transverse to the first direction and is sealed off against the opening by a breakable foil.

17. The device as claimed in claim 1, characterized in that the container is made of plastic.

18. The device as claimed in claim 1, characterized in that the container has a plurality of areas which are joined together in one piece and which each have a first opening for an applicator and associated further openings arranged transverse to the first direction with substance supplies enclosed by breakable foils.

19. The device as claimed in claim 18, characterized in that at least some hollow spaces of the areas are connected to one another.

20. The device as claimed in claim 18, characterized in that at least some of the substance supplies are enclosed by continuous foil pouches.

21. The device as claimed in claim 18, characterized in that the areas have different numbers of further openings and substance supplies.

22. The device as claimed in claim 1, characterized in that it comprises several containers which can be joined together by plug or lock connections.

23. The device as claimed in claim 1, characterized in that the container is substantially cylindrical.

24. The device as claimed in claim 1, characterized in that the container is substantially pyramid-shaped.

25. The device as claimed in claim 1, characterized in that the container is substantially cuboid.

26. The device as claimed in claim 1, characterized in that a further component is arranged within the container.

27. The device as claimed in claim 1, characterized in that it comprises an applicator.

28. The device as claimed in claim 27, characterized in that the applicator is secured on the container with a lock element, and the first opening is closed by a stopper.

29. The device as claimed in claim 27, characterized in that the applicator comprises a brush or a sponge.

30. The device as claimed in claim 27, characterized in that the applicator comprises a spatula.

31. The device as claimed in claim 30, characterized in that the spatula is provided at one end with a stopper for closing the first opening.

32. The device as claimed in claim 27, characterized in that the applicator is impregnated with a further substance.

33. The device as claimed in claim 27, characterized in that the applicator closes the first opening in a leaktight manner.

34. The device as claimed in claim 27, characterized in that the applicator is conical in the front part.

35. The device as claimed in claim 27, characterized in that the applicator is secured with a form fit on the first opening.

36. The device as claimed in claim 27, characterized in that the applicator is connected to the container via a predetermined break point.

37. The device as claimed in claim 1, characterized in that a tube for receiving the applicator is provided on the first opening.

38. The device as claimed in claim 1, characterized in that the container has a bottom surface for setting it down on a base.

39. The device as claimed in claim 1, characterized in that the container has a support, particularly a three-point support for setting it down on a base.

40. The device as claimed in claim 1, characterized in that the second opening is provided with axially extending ribs for supporting the applicator in such a manner that venting passages are present when the applicator is inserted.

41. The device as claimed in claim 1, characterized in that a venting channel is provided at the wall of the second opening.

42. The device as claimed in claim 1, characterized in that the second opening is provided with a stop, preferably an annular stop for the applicator.

43. The device as claimed in claim 1, characterized in that the wall of the container is provided with an outside trough or depression which surrounds the second opening.

44. The device as claimed in claim 43, characterized in that the trough or depression essentially has an oblique conical form with the largest depth in the vicinity of the second opening.

45. The device as claimed in claim 43, characterized in that the second opening is provided with cuttings edges.

46. The device as claimed in claim 1, characterized in that the second opening is surrounded by an annular protrusion for crimping the breakable foil around the opening.

* * * * *

UNITED STATES PATENT AND TRADEMARK OFFICE
CERTIFICATE OF CORRECTION

| | | |
|---|---|---|
| PATENT NO. | : 8,491,211 B2 | Page 1 of 1 |
| APPLICATION NO. | : 12/069101 | |
| DATED | : July 23, 2013 | |
| INVENTOR(S) | : Hans Hörth et al. | |

It is certified that error appears in the above-identified patent and that said Letters Patent is hereby corrected as shown below:

On the Title Page:

Item (30) Foreign Application Priority Data

Insert --(30) This patent claims the priority of German Patent Application No. 10 2005 037 890.0 filed on August 10, 2005.--

Signed and Sealed this
Eighth Day of October, 2013

Teresa Stanek Rea
*Deputy Director of the United States Patent and Trademark Office*